US010005714B2

(12) United States Patent
Tanagi et al.

(10) Patent No.: US 10,005,714 B2
(45) Date of Patent: Jun. 26, 2018

(54) (METH)ACRYLIC ACID ESTER COMPOUND AND PRODUCTION METHOD THEREFOR

(71) Applicant: Mitsubishi Gas Chemical Company, Inc., Tokyo (JP)

(72) Inventors: Hiroyuki Tanagi, Tokyo (JP); Hiroshi Horikoshi, Tokyo (JP); Kikuo Furukawa, Tokyo (JP); Shoichi Hayakawa, Mie (JP); Hiroyasu Tanaka, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days. days.

(21) Appl. No.: 15/118,063

(22) PCT Filed: Feb. 12, 2015

(86) PCT No.: PCT/JP2015/053863
§ 371 (c)(1),
(2) Date: Aug. 10, 2016

(87) PCT Pub. No.: WO2015/122468
PCT Pub. Date: Aug. 20, 2015

(65) Prior Publication Data
US 2017/0008830 A1 Jan. 12, 2017

(30) Foreign Application Priority Data
Feb. 14, 2014 (JP) .................................. 2014-026211

(51) Int. Cl.
| | | |
|---|---|---|
| C07C 69/757 | (2006.01) |
| C08F 220/28 | (2006.01) |
| C09D 133/14 | (2006.01) |
| G03F 7/039 | (2006.01) |
| G03F 7/32 | (2006.01) |
| G03F 7/40 | (2006.01) |
| C07C 67/08 | (2006.01) |
| G03F 7/16 | (2006.01) |
| G03F 7/20 | (2006.01) |

(52) U.S. Cl.
CPC ............ *C07C 69/757* (2013.01); *C07C 67/08* (2013.01); *C08F 220/28* (2013.01); *C09D 133/14* (2013.01); *G03F 7/0397* (2013.01); *G03F 7/162* (2013.01); *G03F 7/2059* (2013.01); *G03F 7/322* (2013.01); *G03F 7/40* (2013.01); *C07C 2603/74* (2017.05); *C08F 2220/282* (2013.01); *C08F 2220/283* (2013.01)

(58) Field of Classification Search
CPC ..... C09D 133/14; C07C 69/757; C07C 67/08; C07C 2603/74; G03F 7/2059; G03F 7/162; G03F 7/322; G03F 7/40; C08G 220/28; C08F 2220/283; C08F 2220/282
See application file for complete search history.

(56) References Cited

U.S. PATENT DOCUMENTS 6,391,520 B1 * 5/2002 Nakano ................ G03F 7/0045
430/270.1
6,656,659 B1 12/2003 Nozaki et al.
2004/0058270 A1 3/2004 Iwai et al.
2005/0266351 A1 12/2005 Takemoto et al.
2012/0196228 A1 8/2012 Nagasawa et al.
2013/0115559 A1 5/2013 Bae et al.

FOREIGN PATENT DOCUMENTS

| JP | H4-39665 A | 2/1992 |
| JP | H10-319595 A | 12/1998 |
| JP | 2000-26446 A | 1/2000 |
| JP | 2003-167346 A | 6/2003 |
| JP | 2004-323704 A | 11/2004 |
| JP | 2005-331918 A | 12/2005 |
| JP | 5409994 B2 | 10/2006 |
| JP | 2008-129388 A | 6/2008 |
| JP | 2011-123143 A | 3/2011 |
| JP | 2012-128009 A | 7/2012 |
| JP | 2012-168502 A | 9/2012 |
| JP | 2013-137513 A | 7/2013 |
| JP | 2014-5339 A | 1/2014 |
| WO | 2011/34007 A1 | 3/2011 |
| WO | 2012/8546 A1 | 1/2012 |
| WO | 2012/101058 A1 | 8/2012 |
| WO | 2013/146081 A1 | 3/2013 |
| WO | 2014/175275 A1 | 10/2014 |

OTHER PUBLICATIONS

Maruyama, Ken et al., "EUV resist development for 16nm half pitch." SPIE Advanced Lithography, Mar. 29, 2012, p. 83250A-83250A, International Society for Optics and Photonics.
Kozawa, Takahiro et al. "Modeling and simulation of acid diffusion in chemically amplified resists with polymer-bound acid generator." Applied Physics Express, Jul. 4, 2012, p. 074301, vol. 5, Issue 7.
Neises, B et al. "Esterification of Carboxylic Acids with Dicyclohexylcarbodiimide/4-Dimethylaminopyridine: tert-Butyl Ethyl Fumarate." Organic Syntheses, Coll. vol. 7, p. 93 (1990); vol. 63, p. 183 (1985).
International Search Report dated May 19, 2015 for PCT/JP2015/053863 and English translation of the same (5 pages).

* cited by examiner

*Primary Examiner* — Cynthia Hamilton
(74) *Attorney, Agent, or Firm* — Fitch, Even, Tabin, & Flannery LLP

(57) ABSTRACT

Provided are a novel alicyclic ester compound and a method for producing a compound of general formula (1) at a high yield from a compound of general formula (2) and a compound of general formula (3). An adamantane compound expressed by general formula (2) and a hydroxyalkyl (meth)acrylate ester compound expressed by general formula (3) are reacted with each other by use of a dehydration condensation agent as a catalyst to obtain an alicyclic ester compound expressed by general formula (1).

6 Claims, No Drawings

(METH)ACRYLIC ACID ESTER COMPOUND AND PRODUCTION METHOD THEREFOR

CROSS-REFERENCE TO RELATED APPLICATIONS

This application is a U.S. national phase application filed under 35 U.S.C. § 371 of International Application PCT/JP2015/053863, filed on Feb. 12, 2015, designating the United States, which claims priority from Japanese Application Number 2014-026211, filed Feb. 14, 2014.

FIELD OF THE INVENTION

The present invention relates to a novel (meth)acrylic ester compound and a method for producing the same, and also relates to a resin and a resin composition synthesized from such an ester compound.

BACKGROUND OF THE INVENTION

A (meth)acrylic ester compound containing adamantane in a chemical structure thereof has high transparency and high heat resistance and is known as being usable for an optical material, a reflection-preventive coat, an optical semiconductor reflecting material, an adhesive, a photoresist and the like (Patent Documents 1 through 3). Such a (meth)acrylic ester compound is in wide use especially for a photoresist among these uses (Patent Documents 4 through 8).

Recently, size reduction is advanced with the lithography process. ArF excimer laser lithography is advanced and now uses liquid immersion exposure and even double patterning exposure. In addition, lithography using extreme ultraviolet (EUV) light, which is a target of attention as a next-generation lithography technology, and electron beam direct drawing, have been developed in various manners.

Although various developments have been made for the purpose of further size reduction, the influence of contrast deterioration caused by diffusion of acid that is generated from a photoacid generator after the exposure has become more serious as the width of the circuit is decreased. Methods for controlling the acid diffusion now proposed include a method of enlarging the structure of the photoacid generator (Non-patent Document 1) and a method of using a resin containing a monomer that contains a photoacid generator (Patent Document 9, Non-patent Document 2). Another method now proposed is a method of extending a pendant part of a resist polymer to block an acid diffusion path (Patent Documents 10 and 11). Patent Documents 12 through 14 propose a photoresist composition that has a superb sensitivity and is capable of reducing the MEEF.

Patent Documents 12 through 14 provide names of chemical substances and chemical structures, but do not describe a production method or the performance as a photoresist regarding a part of the compounds.

A reaction of generating an ester bond from carboxylic acid and alcohol uses a dehydration condensation agent such as a carbodiimide compound or the like. This reaction is known as also esterifying a tertiary hydroxyl group (Patent Document 15, Non-patent Document 3).

PRIOR ART DOCUMENTS

Patent Documents

Patent Document 1: WO2013/146081
Patent Document 2: JP Patent Publication No. 2014-5339
Patent Document 3: JP Patent No. 5409994
Patent Document 4: JP Patent Publication No. H04-39665
Patent Document 5: JP Patent Publication No. H10-319595
Patent Document 6: JP Patent Publication No. 2000-26446
Patent Document 7: JP Patent Publication No. 2003-167346
Patent Document 8: JP Patent Publication No. 2004-323704
Patent Document 9: JP Patent Publication No. 2012-168502
Patent Document 10: JP Patent Publication No. 2005-331918
Patent Document 11: JP Patent Publication No. 2008-129388
Patent Document 12: WO2011/34007
Patent Document 13: JP Patent Publication No. 2011-123143
Patent Document 14: WO2012/8546
Patent Document 15: WO2012/101058

Non-Patent Documents

Non-patent Document 1: SPIE, 8325-10 (2012)
Non-patent Document 2: SPIE, 8322-05 (2012)
Non-patent Document 3: Org. Synth. Coll. Vol. 7:93

SUMMARY OF THE INVENTION

An object of the present invention is to provide a compound of general formula (1a) and a method for producing the compound of general formula (1a) at a high yield.

Another object of the present invention is to provide a resin containing the compound of general formula (1a) as a material and also a photosensitive resin composition containing such a resin as a material.

As a result of active studies made to achieve the above-described objects, the present inventors found that a compound of general formula (1a) is synthesized at a high yield from a compound of general formula (2a) and a compound of general formula (3a) used as materials even by use of a dehydration condensation agent, and thus achieved the present invention. The present invention is as follows.

<1> A (meth)acrylic ester compound expressed by general formula (1a).

[Chemical formula 1]

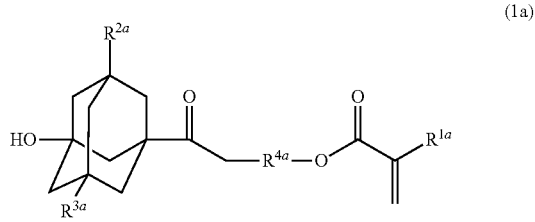

(1a)

In the formula, $R^{1a}$ represents a hydrogen atom or a methyl group, $R^{2a}$ and $R^{3a}$ may be the same as, or different from, each other and independently represent a hydrogen atom, a hydroxyl group, a cyclic, linear or branched alkyl group, aryl group or cycloalkyl group having a carbon number of 1 to 10, an alkoxy group having a carbon number of 1 to 10, an aryloxy group, an acyloxy group having a carbon number of 2 to 6, or a halogen group, and $R^{4a}$ represents a linear or branched alkylene group having a carbon number of 2 to 5.

<2> A method for producing the (meth)acrylic ester compound expressed by general formula (1a) according to <1>, the method comprising reacting an adamantane compound expressed by general formula (2a) with a hydroxyalkyl (meth)acrylate ester compound expressed by general formula (3a) by use of a dehydration condensation agent.

[Chemical formula 2]

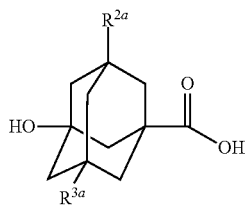

(2a)

In the formula, $R^{2a}$ and $R^{3a}$ are the same as those in chemical formula (1a).

[Chemical formula 3]

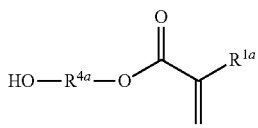

(3a)

In the formula, $R^{1a}$ and $R^{4a}$ are the same as those in chemical formula (1a).

<3> The method according to <2>, wherein the dehydration condensation agent is at least one selected from the group consisting of N,N'-dicyclohexylcarbodiimide, N,N'-diisopropylcarbodiimide, 1-ethyl-3-(3-dimethylaminopropyl)carbodiimidehydrochloride, 2,4,6-trichlorobenzoylchloride, 2-methyl-6-nitrobenzoic anhydride, 2,4,6-trichlorobenzoylchloride, bis(pentafluorophenyl) carbonate, and dimesitylammonium pentafluorobenzenesulfonate.

<4> A (meth)acrylic copolymer, comprising a repeat unit expressed by general formula (4a).

[Chemical formula 4]

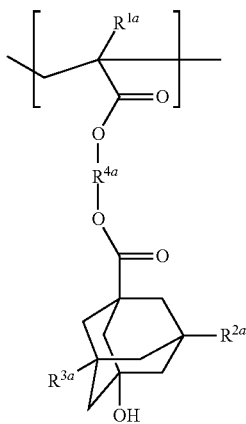

(4a)

In the formula, $R^{1a}$ through $R^{4a}$ are the same as those in chemical formula (1a).

<5> The (meth)acrylic copolymer according to <4>, further comprising a repeat unit expressed by general formula (5a) or (6a) and a repeat unit expressed by general formula (7a) or (8a).

[Chemical formula 5]

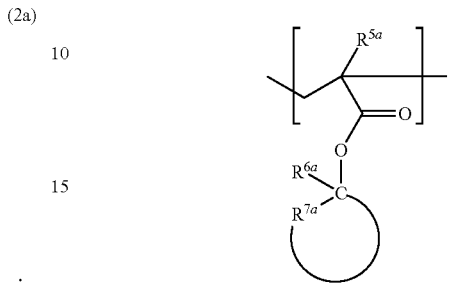

(5a)

In the formula, $R^{5a}$ represents hydrogen or a methyl group, $R^{6a}$ represents an alkyl group having a carbon number of 1 to 4, and $R^{7a}$ represents a linear or branched alkylene group having a carbon number of 5 to 20, or an alicyclic alkylene group.

[Chemical formula 6]

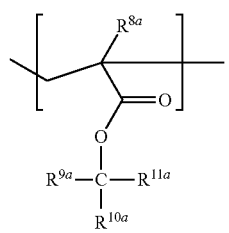

(6a)

In the formula, $R^{8a}$ represents hydrogen or a methyl group, $R^{9a}$ and $R^{10a}$ may be the same as, or different from, each other and each represent an alkyl group having a carbon number of 1 to 4, and $R^{11a}$ represents an alkyl group having a carbon number of 1 to 4, a cycloalkyl group having a carbon number of 5 to 20, or an alicyclic alkyl group.

[Chemical formula 7]

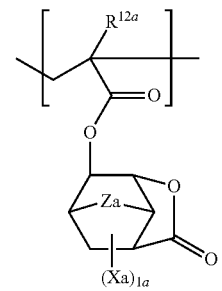

(7a)

In the formula, $R^{12a}$ represents hydrogen or a methyl group, Za represents methylene(-$CH_2$—) or oxa(-O—), Xa(s) may be the same as, or different from, each other and each represent a hydroxyl group, a halogen group, a nitrile group, a carboxylic acid group, an alkyl carboxylate group having a carbon number of 1 to 4, or an alkoxide group having a carbon number of 1 to 4, and l represents an integer of 0 to 2.

[Chemical formula 8]

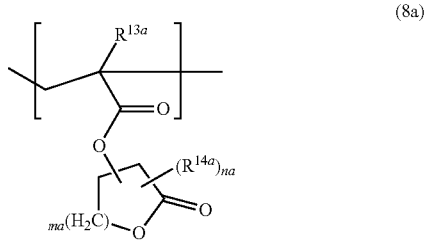

(8a)

In the formula, $R^{13a}$ represents hydrogen or a methyl group, "ma" represents an integer of 1 to 3, $R^{14a}$ represents a methyl group, an ethyl group, a hydroxyl group or a halogen group, and "na" represents an integer of 0 to 2.

<6> A photosensitive resin composition, comprising the (meth)acrylic copolymer according to <4> or <5> and a photoacid generator.

A production method according to the present invention produces a compound of general formula (1a) from a compound of general formula (2a) and a compound of general formula (3a) at a high yield.

The present invention provides a resin containing the compound of general formula (1a) as a material and a photosensitive resin composition containing such a resin as a material.

DESCRIPTION OF EMBODIMENTS

Hereinafter, the present invention will be described in more detail. A (meth)acrylic ester compound according to the present invention is expressed by general formula (1b).

The (meth)acrylic ester compound according to the present invention that is expressed by general formula (1b) is obtained by, for example, reacting an adamantane compound expressed by general formula (2b) with hydroxyalkyl (meth)acrylate ester compound expressed by general formula (3b).

[Chemical formula 9]

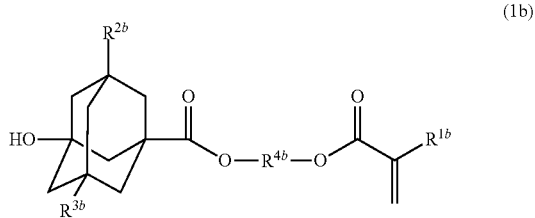

(1b)

In the formula, $R^{1b}$ represents a hydrogen atom or a methyl group, $R^{2b}$ and $R^{3b}$ may be the same as, or different from, each other and independently represent a hydrogen atom, a hydroxyl group, a cyclic, linear or branched alkyl group, aryl group or cycloalkyl group having a carbon number of 1 to 10, an alkoxy group having a carbon number of 1 to 10, an aryloxy group, an acyloxy group having a carbon number of 2 to 6, or a halogen group, and $R^{4b}$ represents a linear or branched alkylene group having a carbon number of 2 to 5.

It is preferable that at least one of $R^{2b}$ and $R^{3b}$ of general formula (1b) is not a hydroxyl group. This is also applicable to the (meth)acrylic ester compound of general formula (1a) above and general formula (1). A (meth)acrylic ester compound as a monol in which neither $R^{2b}$ nor $R^{3b}$ is a hydroxyl group or as a diol in which either $R^{2b}$ or $R^{3b}$ is a hydroxyl group has an appropriate polarity. Therefore, a photosensitive resin composition containing a (meth)acrylic copolymer that contains such a (meth)acrylic ester compound is recognized to have the following effects. A photosensitive resin composition containing a (meth)acrylic copolymer having an appropriate polarity suppresses the water solubility of a part not exposed by an alkali development step to be significantly lower than that of an exposed part, and thus prevents the resist film loss and the dissolution of a pattern. A (meth)acrylic copolymer having an appropriate polarity also has a superb solubility in representative resist solvents, for example, propyleneglycol monomethylether acetate (PGMEA) and propyleneglycol monomethyl ether (PGME), cyclohexane.

The (meth)acrylic ester compound as the above-described monol or diol is usually available more easily than, for example, a triol. In addition, a reaction of generating an adamantane compound as a monol or a diol (see chemical formula (2b) below) easily introduces a single carboxyl group selectively into the adamantane backbone.

The (meth)acrylic ester compound of general formula (1b) includes a part having a low polarity with certainty because $R^{4b}$ is an alkylene group having a relatively long chain with a carbon number of 2 to 5. Therefore, the (meth)acrylic ester compound of general formula (1b) prevents the above-described diffusion of acid generated from a photoacid generator. For these reasons, a photosensitive resin compound containing the (meth)acrylic ester compound of general formula (1b) realizes selective exposure of only a necessary region, and thus has a low limiting resolution and a high sensitivity.

[Chemical formula 10]

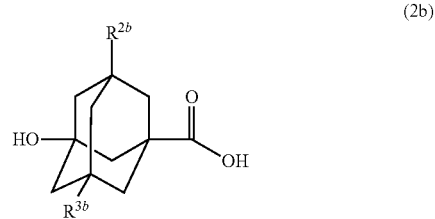

(2b)

In the formula, $R^{2b}$ and $R^{3b}$ are the same as those in chemical formula (1b).

[Chemical formula 11]

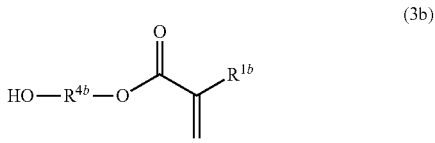

(3b)

In the formula, $R^{1b}$ and $R^{4b}$ are the same as those in chemical formula (1b).

Examples of the alicyclic ester compound expressed by general formula (1b) according to the present invention specifically include 2-(meth)acryloyloxyethyl 3-hydroxy-1-adamantanecarboxylate, 1-(meth)acryloyloxypropane-2-yl 3-hydroxy-1-adamantanecarboxylate, 2-(meth)acryloyloxypropyl 3-hydroxy-1-adamantanecarboxylate, 3-(meth)acryloyloxypropyl 3-hydroxy-1-adamantanecarboxylate, 2-(meth)acryloyloxyethyl 3-hydroxy-5,7-dimethyl-1-adamantanecarboxylate, 2-(meth)acryloyloxyethyl 3-hydroxy-5-ethyl-1-adamantanecarboxylate, 2-(meth)acryloyloxyethyl 3,5-dihydroxy-1-adamantanecarboxylate, 2-(meth)acryloyloxyethyl 3-chloro-5-hydroxy-1-adamantanecarboxylate, and 4-(meth)acryloyloxybutyl 3-hydroxy-1-adamantanecarboxylate.

Examples of the adamantane compound expressed by general formula (2b) usable in the present invention specifically include 3-hydroxy-1-adamantanecarboxylic acid, 5,7-dimethyl-3-hydroxy-1-adamantanecarboxylic acid, 5-ethyl-3-hydroxy-1-adamantanecarboxylic acid, 3,5-dihydroxy-1-adamantanecarboxylic acid, and 3-chloro-5-hydroxy-1-adamantanecarboxylic acid.

Examples of the hydroxyalkyl (meth)acrylate ester compound expressed by general formula (3b) usable in the present invention specifically include 2-hydroxyethyl (meth)acrylate, 2-hydroxypropyl (meth)acrylate, 1-hydroxypropane-2-yl (meth)acrylate, and 4-hydroxybutyl (meth)acrylate. The hydroxyalkyl (meth)acrylate ester compound is incorporated, with respect to the adamantane compound expressed by general formula (2b), at 0.50 to 10.0 equivalent, preferably at 0.8 to 5.0 equivalent, or more preferably at 1.0 to 3.0 equivalent. With such a range of amount of the hydroxyalkyl (meth)acrylate ester compound, neither the adamantane compound expressed by general formula (2b) nor the hydroxyalkyl (meth)acrylate ester compound, which are costly, remains unreacted in a large amount and thus is economically preferable, and the reaction progresses rapidly and thus the purification is performed easily.

The reaction of the adamantane compound expressed by general formula (2b) and the hydroxyalkyl (meth)acrylate ester compound expressed by general formula (3b) is preferably performed by use of a hydration condensation agent.

An acid halogenation method halogenates a hydroxyl group of the adamantane compound expressed by general formula (2b) contained as a material.

Hydration condensation performed with an acid has a very low yield. Reasons why the yield is low are that a compound of general formula (2b) contains a tertiary hydroxyl group in addition to the carboxyl group and that a compound of general formula (3b) contains an ester bond in addition to the hydroxyl group at the end. It is considered that for these reasons, in the case where it is attempted to react the carboxyl group in the compound of general formula (2b) with the hydroxyl group at the end of the compound of general formula (3b), various side reactions occur. The side reactions that may occur include a reaction of the hydroxyl group in the compound of general formula (2b) and the carboxyl group in the compound of general formula (2b), a transesterification reaction of the ester bond in the compound of general formula (3b) and the carboxyl group or the hydroxyl group in the compound of general formula (2b), and hydrosysis of the hydroxyalkyl (meth)acrylate ester compound expressed by general formula (3b).

Specific examples of the dehydration condensation agent usable in the present invention include carbodiimide-based dehydration condensation agents such as N,N'-dicyclohexylcarbodiimide, N,N'-diisopropylcarbodiimide, 1-ethyl-3-(3-dimethylaminopropyl)carbodiimidehydrochloride and the like; mixed acid anhydride-derived dehydration condensation agents such as 2,4,6-trichlorobenzoylchloride, 2-methyl-6-nitrobenzoic anhydride, 2,4,6-trichlorobenzoylchloride, and the like; and active ester-derived dehydration condensation agents such as bis(pentafluorophenyl) carbonate and the like. The dehydration condensation agent is incorporated, with respect to the adamantane compound, at 1.0 to 10.0 equivalent, preferably at 1.1 to 5.0 equivalent, or more preferably at 1.3 to 3.0 equivalent. With such a range of amount of the dehydration condensation agent, the reaction progresses sufficiently, and there is no need to remove an excessive amount of the dehydration condensation agent, which is preferable. Alternatively, an esterification condensation catalyst is preferably usable. A specific example of the esterification condensation catalyst is dimesitylammoniumpentafluorobenzenesulfonate. The esterification condensation catalyst is incorporated, with respect to the adamantane compound, preferably at 0.001 to 0.1 equivalent, or more preferably at 0.005 to 0.5 equivalent. With such a range of amount of the esterification condensation catalyst, the reaction progresses sufficiently, which is economically preferable.

In the case where a carbodiimide-based dehydration condensation agent is used, it is preferable to also use a promoter. Specific examples of the usable promoter include pyridine, 4-dimethylaminopyridine, 1-hydroxybenzotriazole, 1-hydroxy-7-azabenzotriazole, N-hydroxysuccinimide, imide N-hydroxy-5-norbornene-2,3-dicarboxylate, and 4-nitrophenol. The promoter is incorporated, with respect to the adamantane compound, at 0.001 to 0.1 equivalent, preferably at 0.005 to 0.8 equivalent, or more preferably at 0.01 to 0.5 equivalent. With such a range of amount of the promoter, the reaction progresses sufficiently, which is economically preferable.

According to the present invention, the reaction of the adamantane compound expressed by general formula (2b) and the hydroxyalkyl (meth)acrylate ester compound expressed by general formula (3b) may be performed by use of a solvent. Specific examples of the usable solvent include dimethylsulfoxide, diethylether, diisopropylether, tetrahydrofuran, dioxane, dimethylacetamide, dimethylformamide, acetonitrile, benzene, toluene, chloroform, chlorobenzene, dichloroethane, dichloromethane, acetone, methyl ethyl ketone, methyl isobutyl ketone, and the like. The solvent to be used varies in accordance with the dehydration condensation agent to be used. In the case where a carbodiimide-based dehydration condensation agent is used, it is preferable to use a solvent having a low dielectric constant. A chlorine-based solvent such as chloroform, dichloroethane, dichloromethane or the like suppresses a rearrangement reaction that results in the formation of acyl urea, which is a side reaction, and thus is more preferable. The solvent is incorporated at 1 to 100 parts by mass, or preferably at 3 to 10 parts by mass, with respect to 1 part by mass of adamantane compound expressed by general formula (2b). Acyl urea is generated by a one-molecule reaction from acyl isourea, which is of an active type. Therefore, it is more preferable that the concentration of the matrix (general formula (2b)) is higher.

Specific conditions for the above-described reaction are to be appropriately set in accordance with the concentration of the matrix or the catalyst to be used. The reaction temperature is −20° C. to 150° C., more preferably −10° C. to 100° C., or more preferably 0° C. to 80° C. The reaction time duration is 10 minutes to 72 hours, preferably 30 minutes to 48 hours, or more preferably 1 hour to 24 hours. The pressure may be normal pressure, reduced pressure or increased pressure. The reaction process may be appropriately selected from processes such as a batch process, a semi-batch process, a continuous process and the like.

For the above-described reaction, a polymerization inhibitor may be used. Any commonly used polymerization inhibitor may be used with no specific limitation. Examples of the preferable polymerization inhibitor include nitroso compounds such as 2,2,6,6-tetramethyl-4-hydroxypiperidine-1-oxyl, N-nitroso phenylhydroxylamine ammonium salt, N-nitroso phenylhydroxylamine aluminum salt, N-nitroso-N-(1-naphtyl)hydroxylamine ammonium salt, N-nitroso diphenylamine, N-nitroso-N-methylaniline, nitrosonaphthol, p-nitorosophenol, N,N'-dimethyl-p-nitrosoaniline and the like; sulfur-containing compounds such as phenothiazine, methylene blue, 2-mercaptobenzoimidazole, and the like; amines such as N,N'-diphenyl-p-phenylenediamine, N-phenyl-N'-isopropyl-p-phenylenediamine, 4-hydroxydiphenylamine, aminophenol, and the like; quinones such as hydroxyquinoline, hydroquinone, methylhydroquinone, p-benzoquinone, hydroquinone monomethyl ether, and the like; phenols such as p-methoxyphenol, 2,4-dimethyl-6-t-butylphenol, catechol, 3-s-butylcatechol, 2,2-methylenebis-(6-t-butyl-4-methylphenol), and the like; imides such as N-hydroxyphthalimide, and the like; oximes such as cyclohexaneoxime, p-quinonedioxime, and the like; dialkylthiodipropinate; and the like. The polymerization inhibitor is incorporated to have a content of 0.001 to 10 parts by weight, or preferably a content of 0.01 to 1 part by weight, with respect to 100 parts by weight of hydroxyalkyl (meth)acrylate ester compound expressed by general formula (3b).

The (meth)acrylic ester compound expressed by general formula (1b) obtained in this manner may be isolated and purified as a high purity monomer by a separation and purification method such as water-washing, filtration, concentration, distillation, extraction, crystallization, re-crystallization, column chromatography, use of activated carbon or the like, or any combination thereof. For example, the reaction solution is washed with water to remove excessive amounts of hydroxyalkyl (meth)acrylate ester compound, catalyst and other additives. In the case where a water-soluble carbodiimide-based dehydration condensation agent such as 1-ethyl-3-(3-dimethylaminopropyl)carbodiimidehydrochloride or the like is used, an excessive amount of the dehydration condensation agent and urea, which is generated by a side reaction, are removed at the same time by water-washing. In this step, the washing water may contain an inorganic salt such as sodium chloride, sodium hydrogen carbonate, sodium carbonate or the like. The washing may be performed with an aqueous solution of sodium hydroxide, which is alkaline. In the case where N,N'-dicyclohexylcarbodiimide or N,N'-diisopropylcarbodiimide is used as the condensation agent, urea generated by a side reaction is removable by filtration. Therefore, an excessive amount of carbodiimide is converted by water washing into urea, and then the urea is removed by filtration. In the case where a (meth)acrylic ester compound is used as a material of a resist monomer, the amount of metal impurities needs to be reduced. Therefore, acid washing may be performed to remove the metal impurities. Usable for the acid washing are, for example, inorganic acid solutions such as an aqueous solution of hydrochloric acid, an aqueous solution of sulfuric acid, an aqueous solution of phosphoric acid, and the like; and organic acid solutions such as an aqueous solution of oxalic acid, and the like. For the washing, an organic solvent or the like may be incorporated. Usually, a solvent that has a low polarity and thus is well separable from water is preferable.

The (meth)acrylic ester compound according to the present invention is preferably usable for a photoresist monomer, an optical material, an optical film, a coat for optical film, and an optical adhesive.

A (meth)acrylic copolymer obtained by copolymerization of the (meth)acrylic ester compound expressed by general formula (1b) according to the present invention is usable for a functional resin used for a photoresist. The (meth)acrylic copolymer according to the present invention preferably includes a repeat unit expressed by general formula (4b), at least one type of repeat unit selected from general formulas (5b) and (6b), and at least one type of repeat unit selected from general formulas (7b) and (8b). The repeat unit of general formula (4b) may be obtained by use of the alicyclic ester compound expressed by general formula (1b) as a material.

[Chemical formula 12]

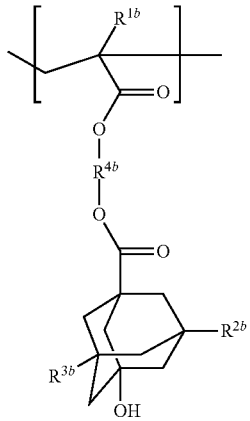

(4b)

In the formula, $R^{1b}$ through $R^{4b}$ are the same as those in general formula (1b).

[Chemical formula 13]

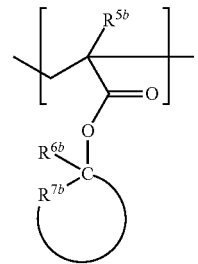

(5b)

In the formula, $R^{5b}$ represents hydrogen or a methyl group, $R^{6b}$ represents an alkyl group having a carbon number of 1 to 4, and $R^{7b}$ represents a linear or branched alkylene group having a carbon number of 5 to 20, or an alicyclic alkylene group.

[Chemical formula 14]

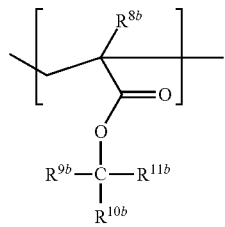

(6b)

In the formula, $R^{8b}$ represents hydrogen or a methyl group, $R^{9b}$ and $R^{10b}$ may be the same as, or different from, each other and each represent an alkyl group having a carbon number of 1 to 4, and $R^{11b}$ represents an alkyl group having a carbon number of 1 to 4, a cycloalkyl group having a carbon number of 5 to 20, or an alicyclic alkyl group.)

[Chemical formula 15]

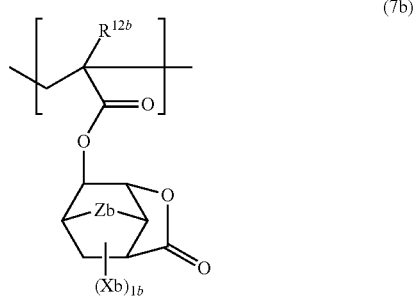

(7b)

In the formula, $R^{12b}$ represents hydrogen or a methyl group, Zb represents methylene(-CH$_2$—) or oxa(-O—), Xb(s) may be the same as, or different from, each other and each represent a hydroxyl group, a halogen group, a nitrile group, a carboxylic acid group, an alkyl carboxylate group having a carbon number of 1 to 4, or an alkoxide group having a carbon number of 1 to 4, and Ib represents an integer of 0 to 2.

[Chemical formula 16]

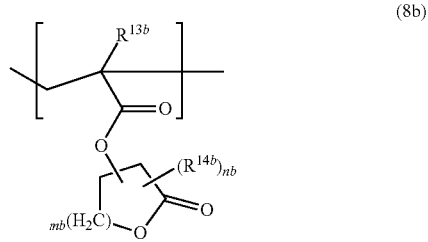

(8b)

In the formula, $R^{13b}$ represents hydrogen or a methyl group, "mb" represents an integer of 1 to 3, $R^{14b}$ represents a methyl group, an ethyl group, a hydroxyl group or a halogen group, and "nb" represents an integer of 0 to 2.

Examples of material of the repeat unit expressed by general formula (5b) include 2-methyl-2-(meth)acryloyloxyadamantane, 2-ethyl-2-(meth)acryloyloxyadamantane, 2-isopropyl-2-(meth)acryloyloxyadamantane, 2-n-propyl-2-(meth)acryloyloxyadamantane, 2-n-butyl-2-(meth)acryloyloxyadamantane, 1-methyl-1-(meth)acryloyloxycyclopentane, 1-ethyl-1-(meth)acryloyloxycyclopentane, 1-methyl-1-(meth)acryloyloxycyclohexane, 1-ethyl-1-(meth)acryloyloxycyclohexane, 1-methyl-1-(meth)acryloyloxycycloheptane, 1-ethyl-1-(meth)acryloyloxycycloheptane, 1-methyl-1-(meth)acryloyloxycyclooctane, 1-ethyl-1-(meth)acryloyloxycyclooctane, 2-ethyl-2-(meth)acryloyloxydecahydro-1,4:5,8-dimethanonaphthalene, 2-ethyl-2-(meth)acryloyloxynorbornane, and the like.

Examples of material of the repeat unit expressed by general formula (6b) include 2-cyclohexyl-2-(meth)acryloyloxypropane, 2-(4-methylcyclohexyl)-2-(meth)acryloyloxypropane, 2,-adamantyl-2-(meth)acryloyloxypropane, 2-(3-(1-hydroxy-1-methylethyl)adamantyl)-2-(meth)acryloyloxypropane, and the like.

Examples of material of the repeat unit expressed by general formula (7b) include 2-(meth)acryloyloxy-5-oxo-4-oxatricyclo[4.2.1.0$^{3,7}$]nonane, 7 or 8-(meth)acryloyloxy-3-oxo-4-oxatricyclo[5.2.1.0$^{2,6}$]decane, 9-(meth)acryloyloxy-3-oxo-2-oxa-6-oxa-tricyclo[4.2.1.0$^{4,8}$]nonane, 2-(meth)acryloyloxy-5-oxo-4-oxa-8-oxatricyclo[4.2.1.0$^{3,7}$]nonane, 2-(meth)acryloyloxy-9-methoxycarbonyl-5-oxo-4-oxatricyclo[4.2.1.0$^{3,7}$]nonane, 2-(meth)acryloyloxy-5-oxo-4-oxatricyclo[4.2.1.0$^{3,7}$]nonane-6-carbonitrile, and the like.

Examples of material of the repeat unit expressed by general formula (8b) include α-(meth)acryloyloxy-γ-butyrolactone, β-(meth)acryloyloxy-γ-butyrolactone, (meth)acryloyloxypantolactone, and the like.

The repeat units expressed by general formulas (5b) and (6b) have a function of being dissociated with an acid. The repeat units expressed by general formulas (5b) and (6b) have approximately an equal level of performance regarding the dissociation. At least one type of such a repeat unit contained in the (meth)acrylic copolymer reacts with an acid generated from a photoacid generator at the time of exposure to generate a carboxylic acid group, and thus the (meth)acrylic copolymer is converted into an alkali-soluble substance.

The repeat units expressed by general formulas (7b) and (8b) each contain a lactone group. The repeat units expressed by generals formulas (7b) and (8b) have approximately an equal level of performance regarding the lactone group. At least one type of such a repeat unit contained in the (meth)acrylic copolymer improves the solubility in a solvent, the adherence to a substrate, and the affinity to an alkaline developer. Thus, the (meth)acrylic copolymer is usable for photolithography.

In the (meth)acrylic copolymer according to the present invention, the repeat unit of general formula (4b) is contained preferably at a ratio of 1% by weight to 60% by weight, preferably at a ratio of 3% by weight to 50% by weight, or more preferably at a ratio of 5% by weight to 40% by weight. At least one type of repeat unit of general formula (5b) or (6b) is contained preferably at a ratio of 10% by weight to 80% by weight, preferably at a ratio of 15% by weight to 60% by weight, or more preferably at a ratio of 20% by weight to 50% by weight. At least one type of repeat unit of general formula (7b) or (8b) is contained preferably at a ratio of 10% by weight to 80% by weight, preferably at a ratio of 15% by weight to 60% by weight, or more preferably at a ratio of 15% by weight to 50% by weight.

The total of the ratios of the repeat unit of general formula (4b), the repeat unit(s) of general formulas (5b) and (6b), and the repeat unit(s) of general formulas (7b) and (8b) is 100% by weight. The (meth)acrylic copolymer according to the present invention may contain any other repeat unit at a ratio of 20% by weight or less, or preferably at a ratio of 10% by weight or less, in addition to the repeat units of general formulas (4b) through (8b).

Generally for polymerization, the monomer as the repeat unit is dissolved in a solvent, a catalyst is added, and the reaction is caused while the substances are heated or cooled. Conditions of the polymerization reaction may be optionally set in accordance with the type of initiator, the method for initiating polymerization by heat, light, and so on, the temperature, the pressure, the concentration, the solvent, the additives and the like. A polymerization reaction for the (meth)acrylic copolymer according to the present invention may be performed by, for example, radical polymerization using a radical generator such as azoisobutyronitrile, peroxide or the like, or ion polymerization using a catalyst such as alkyllithium, a Grignard reagent or the like.

Examples of the solvent usable for the polymerization reaction for the (meth)acrylic copolymer according to the present invention include ketones such as 2-butanone, 2-heptanone, methylisobutylketone, cyclohexanone and the like; alkanes such as hexane, heptane, octane, cyclohexane, cyclooctane, decalin, norbornane and the like; alcohols such as methanol, ethanol, propanol, 2-propanol, n-butanol, sec-butanol, t-butanol, pentanol, hexanol, propyleneglycol monomethylether, and the like; ethers such as diethylether, tetrahydrofuran, 1,4-dioxane, and the like; and carboxylic acid esters such as ethyl acetate, butyl acetate, methyl lactate, propyleneglycol monomethylether acetate, and the like. These solvents may be used independently or in a combination of two or more thereof.

The (meth)acrylic copolymer obtained by the present invention may be purified by a known method. Specifically, metal impurities may be removed by a combination of any of ultrafiltration, precision filtration, acid washing, water washing with an electric conductivity of 10 mS/m. or less, and extraction. In the case where acid washing is performed, a water-soluble acid may be used, for example, an organic acid such as formic acid, acetic acid, propionic acid or the like, or an inorganic acid such as hydrochloric acid, sulfuric acid, nitric acid, phosphoric acid or the like. In consideration of the separability from the reaction solution, it is preferable to use an inorganic acid. For removing an oligomer, any of ultrafiltration, precision filtration, crystallization, re-crystallization, extraction, water washing with an electric conductivity of 10 mS/m. or less, and the like may be combined.

The (meth)acrylic copolymer according to the present invention has a polystyrene-converted weight-average molecular weight (hereinafter, referred to as "Mw") measured by gel permeation chromatography (GPC) of preferably 1,000 to 500,000, or more preferably 3,000 to 100,000. The ratio of Mw with respect to a polystyrene-converted number-average molecular weight (hereinafter, referred to as "Mn") measured by GPC, namely, Mw/Mn, of the (meth) acrylic copolymer is usually 1 to 10, or preferably 1 to 5. According to the present invention, a single type of (meth) acrylic copolymer may be used, or two or more types of (meth)acrylic copolymer may be used in combination.

The (meth)acrylic copolymer according to the present invention may be used as a material of a photosensitive resin composition.

The photosensitive resin composition may be used as a photoresist. The photosensitive resin composition has superb adherence to the substrate and is alkali-soluble, and thus is formed into a minute pattern at high precision.

Such a photosensitive resin composition according to the present invention may contain the above-described (meth) acrylic copolymer and a photoacid generator that are dissolved in a solvent. Examples of the commonly usable solvent include linear ketones such as 2-pentanone, 2-hexanone and the like; cyclic ketones such as cyclopentanone, cyclohexanone, and the like; propyleneglycol monoalkyl acetates such as propyleneglycol monomethylether acetate, propyleneglycol monoethylether acetate, and the like; ethyleneglycol monoalkylether acetates such as ethyleneglycol monomethylether acetate, ethyleneglycol monoethylether acetate, and the like; propyleneglycol monoalkylethers such as propyleneglycol monomethylether, propyleneglycol monoethylether, and the like; ethyleneglycol monoalkylethers such as ethyleneglycol monomethylether, ethyleneglycol monoethylether, and the like; diethyleneglycol alkylethers such as diethyleneglycol dimethylether, diethyleneglycol diethylether, and the like; esters such as ethyl acetate, ethyl lactate, and the like; alcohols such as cyclohexanol, 1-octanol, and the like; ethylene carbonate; γ-butyrolactone; and the like. These solvents may be used independently or in a combination of two or more thereof.

As the photoacid generator, any substance appropriate for the wavelength of the exposing light may be selected from substances usable as an acid generator for a chemical amplification resist composition, in consideration of the range of thickness of the resist film and the optical absorption coefficient of the substance. A single type of photoacid generator may be used, or two or more types of photoacid generator may be used in combination. The photoacid generator is contained preferably at 0.1 to 20 parts by weight, or more preferably at 0.5 to 15 parts by weight, with respect to 100 parts by weight of (meth)acrylic copolymer.

Examples of the photoacid generator usable in a far ultraviolet region include onium salt compound, sulfoneimide compound, sulfone compound, sulfonic acid ester compound, quinonediazide compound, diazomethane compound, and the like. Among these photoacid generators, examples of the photoacid generator preferable for a KrF excimer laser, EUV light and an electron beam include onium salt compounds such as sulfonium salt, iodonium salt, phosphonium salt, diazonium salt, pyridinium salt, and the like. Specific examples of such a preferable photoacid generator include triphenylsulfonium trifluoromethanesulfonate, triphenylsulfonium nonafluorobutyrate, triphenylsulfonium hexafluoroantimonate, triphenylsulfonium naphthalenesulfonate, (hydroxyphenyl)benzylmethylsulfonium toluenesulfonate, diphenyliodonium trifluoromethanesulfonate, diphenyliodonium pyrenesulfonate, diphenyliodonium dodecylbenzenesulfonate, diphenyliodonium hexafluoroantimonate, and the like.

The photosensitive resin composition according to the present invention may contain an acid diffusion controller. The acid diffusion controller is contained for the purpose of controlling the phenomenon that an acid generated from the photoacid generator by exposure is diffused in a resist film and thus suppressing a non-preferable chemical reaction in a non-exposed region.

A preferable acid diffusion controller is a nitrogen-containing organic compound which does not have a basicity thereof changed by exposure or heating performed during the formation of a resist pattern. Examples of such a nitrogen-containing organic compound include monoalkylamines such as n-hexylamine, n-heptylamine, n-octylamine, and the like; dialkylamines such as di-n-butylamine, and the like; trialkylamines such as trimethylamine, and the like; substituted trialcoholamines such as triethanolamine, tripropanolamine, tributanolamine, tripentanolamine, trihexanolamine, and the like; trialkoxyalkylamines such as trimethoxyethylamine, trimethoxypropylamine, trimethoxybutylamine, triethoxybutylamine, and the like; aromatic amines such as aniline, N,N-dimethylaniline, 2-methylaniline, 3-methylaniline, 4-methylaniline, 4-nitroaniline, diphenylamine, and the like; amine compounds such as ethylenediamine, and the like; amide compounds such as formamide, N,N-dimethylformamide, N,N-dimethylacetamide, N-methylpyrrolidone, and the like; urea compounds such as urea, and the like; imidazoles such as imidazole, benzimidazole, and the like; pyridines such as pyridine, 4-methylpyridine, and the like; 1,4-diazabicyclo[2.2.2]octane; and the like. The acid diffusion controller is contained generally at 15 parts by weight or less, preferably at 0.001 to 10 parts by weight, or more preferably at 0.005 to 5 parts by weight, with respect to 100 parts by weight of (meth)acrylic copolymer.

The photosensitive resin composition according to the present invention may also contain any of various additives, for example, a surfactant, a quencher, a sensitizer, a halation inhibiting agent, a preservative/stabilizer, a defoamer, and the like.

The photosensitive resin composition according to the present invention is formed into a resist pattern as follows. The photosensitive resin composition according to the present invention is applied to a substrate formed of, for example, a silicon wafer, a metal material, a plastic material, glass, a ceramic material or the like by use of an appropriate application device such as a spin coater, a dip coater, a roller coater or the like to form a resist film. The resist film is optionally pre-heated at a temperature of about 50° C. to 200° C., and then is exposed to light via a predetermined mask pattern.

The resist film has an approximate thickness of, for example, 0.01 to 5 μm, preferably 0.02 to 1 μm, or more preferably 0.02 to 0.1 μm. The exposure may be performed by use of a light beam having any of various wavelengths appropriately selected from, for example, far ultraviolet light generated from an $F_2$ excimer laser (wavelength: 157 nm), an ArF excimer laser (wavelength: 193 nm) or a KrF excimer laser (wavelength: 248 nm) or the like, EUV light (wavelength: 13 nm), an X-ray, an electronic beam and the like. Exposure conditions including the exposure amount are appropriately selected in accordance with the composition of the photosensitive resin composition, the type of additives and the like.

In the present invention, it is preferable that the heating is performed after the exposure at a temperature of 50 to 200° C. for 30 seconds or longer in order to form a highly precise minute pattern stably. When the temperature is lower than 50° C., there is an undesirable possibility that the sensitivity is largely dispersed in accordance with the type of the substrate. After the heating, development is performed with an alkaline developer usually at 10 to 50° C. for 10 to 200 seconds, or preferably at 20 to 25° C. for 15 to 1200 seconds. In this manner, a predetermined resist pattern is formed.

An example of usable alkaline developer is an alkaline aqueous solution containing an alkaline compound dissolved so as to have a concentration of usually 0.0001 to 10% by weight, preferably 0.01 to 5% by weight, or more preferably 0.1 to 3% by weight. Examples of the alkaline compound include alkali metal hydroxide, ammonia water, alkylamines, alkanolamines, heterocyclic amines, tetraalkylammoniumhydroxides, choline, 1,8-diazabicyclo-[5.4.0]-7-undecene, 1,5-diazabicyclo-[4.3.0]-5-nonene, and the like. The developer containing the alkaline aqueous solution may also optionally contain a water-soluble organic solvent or a surfactant.

EXAMPLES

Hereinafter, the present invention will be specifically described by way of examples. The present invention is not limited to any of the following examples. In the examples, the purity and the yield of the (meth)acrylic ester compound were determined by gas chromatography (GC) or high performance liquid chromatography (HPLC), and the structure thereof was determined by $^1H$ and $^{13}C$-NMR. A gas chromatograph mass spectrometer was used to measure the m/z of each of components. The HPLC measurement conditions were as follows.
<HPLC Measurement Conditions>
Column: L-column ODS L-C18 (5 μm, 4.6φ×250 mm) of Chemicals Evaluation and Research Institute, Japan; developing solvent: methanol/water=40/60 (v/v); flow rate: 1 ml/minute; column temperature: 40° C.; detector: R1
<GC Conditions>
Column: TC-17 (0.53 mm I.D.×30 m); injection temperature: 280° C.; oven temperature: 70° C. (kept for 1 minute→raised at 10° C./min.→280° C. (kept for 10 minutes); detector: FID; transfer phase: helium Example 1

Production of 2-methacryloyloxyethyl 3-hydroxy-1-adamantanecarboxylate (Monomer A1)

A 500 ml jacketed reactor provided with a stirrer and a thermometer was supplied with 19.58 g (0.10 mol) of 3-hydroxy-1-adamantanecarboxylic acid, 19.55 g (0.15 mol) of 2-hydroxyethyl methacrylate, 2.44 g (0.02 mol) of 4-dimethylaminopyridine, and 100 ml of dichloroethane, and the temperature of the liquid was lowered to 12° C. 28.78 g (0.15 mol) of 1-ethyl-3-(3-dimethylaminopropyl)carbodiimidehydrochloride was added thereto, and the resultant substance was stirred at 12° C. for 6 hours. Then, the cooling was stopped, and the substance was stirred at room temperature for 16 hours. 2-methacryloyloxyethyl 3-hydroxy-1-adamantanecarboxylate, which was the product, was confirmed by GC to be produced at a reaction yield of 95.7%. After the reaction was finished, 160 g of diisopropylether was added, and the organic layer was washed with 200 g of ion exchange water, washed twice with 200 g of 5% aqueous solution of sodium carbonate, washed with 200 g of 1% aqueous solution of sulfuric acid, and washed with 200 g of ion exchange water. The organic layer was recovered, 30 mg of p-methoxyphenol was added, and the solvent was concentrated in vacuum. As a result, 8.96 g of orange viscous liquid was obtained (yield: 93.9%). This compound was confirmed by an NMR measurement to be 2-methacryloyloxyethyl 3-hydroxy-1-adamantanecarboxylate.

$^1H$-NMR spectrum (CDCl$_3$): δ1.5 to 1.9 ppm (14H, adamantane), 2.2 ppm (3H, methyl group of methacryloyl group), 4.30 ppm to 4.32 ppm (4H, —O—(CH$_2$)$_2$—O—), 5.6 ppm (1H, double bond of methacryloyl group), 6.1 ppm (1H, double bond of methacryloyl group). $^{13}C$-NMR spectrum (CDCl$_3$): 15.3 ppm (methyl group of methacryloyl group), 27.2, 32.0, 34.6, 41.1, 43.1 ppm (adamantane), 59.1, 59.3 ppm (—O—(CH$_2$)$_2$—O—), 69.2 ppm (OH-bond of adamantane), 123.2 ppm (terminus of double bond of methacryloyl group), 132.9 ppm (carbonyl a position of methacryloyl group), 164.2 ppm (methacryloyl group carbonyl group), 173.2 ppm (carbonyl adamantanecarboxylate group).

Example 2

Production of 2-methacryloyloxyethyl 3-hydroxy-1-adamantanecarboxylate

A 300 ml three-necked round bottom flask provided with a stirrer and a thermometer was supplied with 9.76 g (0.075 mol) of 2-hydroxyethyl methacrylate and 50 ml of 1,2-dichloroethane, and then was supplied with 9.81 g (0.05 mol) of 3-hydroxy-1-adamantanecarboxylic acid and 1.22 g (0.01 mol) of 4-dimethylaminopyridine. The temperature of the oil bath was set to 40° C., and the oil bath was heated until the liquid temperature became 39° C. 14.4 g (0.075 mol) of 1-ethyl-3-(3-dimethylaminopropyl)carbodiimidehydrochloride was added thereto, and the resultant substance was stirred at 39° C. for 5 hours. Then, the heating was stopped, and the substance was stirred at room temperature for 16 hours. 2-methacryloyloxyethyl 3-hydroxy-1-adamantanecarboxylate, which was the product, was confirmed by GC to be produced at a reaction yield of 94.2%. After the reaction was finished, 80 g of diisopropylether was added, and the organic layer was washed with 100 g of ion exchange water, washed twice with 100 g of 5% aqueous solution of sodium carbonate, washed with 100 g of 1% aqueous solution of sulfuric acid, and washed with 100 g of ion exchange water. The organic layer was recovered, 15 mg of p-methoxyphenol was added, and the solvent was concentrated in vacuum. As a result, 14.45 g of orange viscous liquid was obtained (yield: 93.7%). This compound was confirmed by an NMR measurement to be 2-methacryloyloxyethyl 3-hydroxy-1-adamantanecarboxylate.

Example 3

Production of 2-methacryloyloxyethyl 3-hydroxy-1-adamantanecarboxylate

A 500 ml jacketed reactor provided with a stirrer and a thermometer was supplied with 9.81 g (0.05 mol) of 3-hydroxy-1-adamantanecarboxylic acid, 9.76 g (0.075 mol) of 2-hydroxyethyl methacrylate, 305 mg (2.5 mmol) of 4-dimethylaminopyridine, and 50 ml of dichloroethane, and the temperature of the liquid was lowered to 12° C. 20.63 g (0.10 mol) of N,N'-dicyclohexylcarbodiimide, was added thereto, and the resultant substance was stirred at 12° C. for 6 hours. Then, the cooling was stopped, and the substance was stirred at room temperature for 16 hours. After the reaction was finished, the resultant substance was filtrated with a 5 C filter to remove the solid, and then 250 ml of toluene was added. The resultant organic layer was washed twice with 100 g of ion exchange water, washed with 100 g of 1% aqueous solution of sulfuric acid, and washed with 100 g of ion exchange water. The organic layer was recovered, filtrated with a 5 C filter to remove the solid, and concentrated. Then, a component having an Rf value of 0.5 was recovered by a silica gel column (developing solvent: hexane/ethyl acetate=1/1 (v/v)). 15 mg of p-methoxyphenol was added, and the solvent was concentrated in vacuum. As a result, 14.10 g of orange viscous liquid was obtained (yield: 91.6%). This compound was confirmed by an NMR measurement to be 2-methacryloyloxyethyl 3-hydroxy-1-adamantanecarboxylate.

Example 4

Production of 1-methacryloyloxypropane-2-yl 3-hydroxy-1-adamantanecarboxylate

A 500 ml jacketed reactor provided with a stirrer and a thermometer was supplied with 9.81 g (0.05 mol) of 3-hydroxy-1-adamantanecarboxylic acid, 10.8 g (0.075 mol) of 2-hydroxypropyl methacrylate, 1.22 g (0.01 mol) of 4-dimethylaminopyridine, and 50 ml of dichloroethane, and the temperature of the liquid was lowered to 12° C. 14.4 g (0.075 mol) of 1-ethyl-3-(3-dimethylaminopropyl)carbodiimidehydrochloride was added thereto, and the resultant substance was stirred at 12° C. for 6 hours. Then, the cooling was stopped, and the substance was stirred at room temperature for 16 hours. After the reaction was finished, 250 ml of toluene was added. The resultant organic layer was washed with 100 g of ion exchange water, washed twice with 100 g of 5% aqueous solution of sodium carbonate, washed with 100 g of 1% aqueous solution of sulfuric acid, and washed with 100 g of ion exchange water. The organic layer was recovered, 15 mg of p-methoxyphenol was added, and the solvent was concentrated in vacuum. As a result, 14.45 g of orange viscous liquid was obtained (yield: 89.8%). This compound was confirmed by an NMR measurement to be 1-methacryloyloxyethyl 3-hydroxy-1-adamantanecarboxylate.

$^1$H-NMR spectrum (CDCl$_3$): δ1.22 to 1.27 ppm (3H, —O—CH(C$\underline{H}_3$)—CH$_2$—O—), 1.5 to 1.9 ppm (14H, adamantane), 2.2 ppm (3H, methyl group of methacryloyl group), 4.15 ppm (2H, —O—CH(CH$_3$)—C$\underline{H}_2$—O—), 5.17 ppm (1H, —O—C$\underline{H}$(CH$_3$)—CH$_2$—O—), 5.6 ppm (1H, double bond of methacryloyl group), 6.1 ppm (1H, double bond of methacryloyl group). $^{13}$C-NMR spectrum (CDCl$_3$): 13.5 ppm (—O—CH(C$\underline{H}_3$)—CH$_2$—O—), 15.3 ppm (methyl group of methacryloyl group), 27.2, 32.0, 34.6, 41.2, 43.2 ppm (adamantane), 62.9 ppm (—O—$\underline{C}$H(CH$_3$)—CH$_2$—O—), 65.3 ppm (OH-bond of adamantane), 73.9 ppm (—O—CH(CH$_3$)—$\underline{C}$H$_2$—O—), 123.2 ppm (terminus of double bond of methacryloyl group), 132.9 ppm (carbonyl a position of methacryloyl group), 164.2 ppm (methacryloyl group carbonyl group), 173.2 ppm (carbonyl adamantanecarboxylate group).

Comparative Example 1

A 300 ml three-necked round bottom flask provided with a stirrer and a thermometer was supplied with 9.81 g (0.05 mol) of 3-hydroxy-1-adamantanecarboxylic acid, and the 3-hydroxy-1-adamantanecarboxylic acid was dissolved in 100 mL of THF. 0.04 g (0.5 mmol) of DMF was added thereto, and nitrogen was blown thereto. 19.04 g (0.15 mol) of oxalylchloride was added thereto, and the resultant substance was stirred. Excessive amounts of oxalylchloride, THF an DMF were removed by distillation in vacuum. A measurement of the infrared spectrum of the residue indicated that a peak of 3000 to 3600 cm$^{-1}$ derived from a hydroxyl group had disappeared. Thus, the hydroxyl group of 3-hydroxy-1-adamantanecarboxylic acid was confirmed to be converted into —Cl.

Comparative Example 2

A 500 ml three-necked round bottom flask provided with a stirrer, a thermometer and a Dean-Stark tube was supplied with 9.81 g (0.05 mol) of 3-hydroxy-1-adamantanecarboxylic acid, 9.76 g (0.15 mol) of 2-hydroxyethyl methacrylate, 200 mL of toluene, and 0.05 g (0.5 mmol) of sulfuric acid. The resultant substance was refluxed at the boiling point for 5 hours while generated water was removed via the Dean-Stark tube. It was confirmed by GC that the conversion ratio of the 3-hydroxy-1-adamantanecarboxylic acid had become 100%. After the reaction was finished, 1-(meth)acryloyloxypropane-2-yl 3-hydroxy-1-adamantanecarboxylate was confirmed by HPLC to be produced at a yield of 23.1%.

Example 5

Resin Synthesis Example 1

3.70 g of 2-methacryloyloxyethyl 3-hydroxy-1-adamantanecarboxylate (hereinafter, referred to as "monomer A1") obtained in Example 1, 5.96 g of 2-ethyl-2-methacryloyloxyadamantane (hereinafter, referred to as "monomer B1"), 4.08 g of α-methacryloyloxy-γ-butyrolactone (hereinafter, referred to as "monomer C1"), and 0.49 g of azobisisobutyronitrile were dissolved in 130 mL of tetrahydrofuran, and polymerization was performed for 15 hours while the reaction temperature was kept at 60° C. in a nitrogen atmosphere (the ratio of monomer amounts was A1/B1/C1=20/40/40 mol %). After the polymerization, the reaction solution was dripped into 650 mL of n-hexane to solidify and purify the resin. The generated white powder was filtrated by a membrane filter and washed with 1000 ml of n-hexane. The white powder was recovered, and dried overnight at 40° C. at reduced pressure. As a result, 9.21 g of methacrylic copolymer P1 was obtained.

Example 6

Resin Synthesis Example 2

2.77 g of 2-methacryloyloxyethyl 3-hydroxy-1-adamantanecarboxylate (monomer A1) obtained in Example 1, 4.72 g of 2-adamantyl-2-methacryloyloxypropane (hereinafter, referred to as "monomer B2"), 4.00 g of 2-methacryloyloxy-5-oxo-4-oxatricyclo[4.2.1.0$^{3,7}$]nonane (hereinafter, referred to as "monomer C2"), and 0.37 g of azobisisobutyronitrile were dissolved in 100 mL of tetrahydrofuran, and polymerization was performed for 15 hours while the reaction temperature was kept at 60° C. in a nitrogen atmosphere (the ratio of monomer amounts was A1/B2/C2=20/40/40 mol %). After the polymerization, the reaction solution was dripped into 500 mL of n-hexane to solidify and purify the resin. The generated white powder was filtrated by a membrane filter and washed with 1000 ml of n-hexane. The white powder was recovered, and dried overnight at 40° C. at reduced pressure. As a result, 10.43 g of methacrylic copolymer P2 was obtained.

Comparative Example 3

The same operation as in Example 5 was performed except that 2.84 g of 3-hydroxy-1-adamantylmethacrylate (hereinafter, referred to as "monomer A2") was used instead of monomer A1 (the ratio of monomer amounts was A2/B1/C1=20/40/40 mol %). As a result, 8.94 g of methacrylic copolymer P3 was obtained.

Synthesis Example 1 (Synthesis of Monomer A3)

A 100 ml three-necked round bottom flask provided with a stirrer, a thermometer and an air inlet was supplied with 49.08 g (0.25 mol) of 3-hydroxy-1-adamantanecarboxylic acid, 31.98 g (0.225 mol) of glycidyl methacrylate, 2.74 g (25 mmol) of tetramethylammoniumchloride, 319.6 mg (2.6 mmol) of p-methoxyphenol, and 250 g of dimethylsulfoxide, and the resultant substance was stirred at 90° C. for 5 hours while air was blown into the flask. After the reaction was finished, 1000 g of chloroform was added thereto, and the organic layer was washed with 1000 g of 5% aqueous solution of sodium chloride, washed with 1000 g of 5% aqueous solution of sodium carbonate, washed with 1000 g of 1% aqueous solution of sulfuric acid, and washed with 1000 g of 5% aqueous solution of sodium chloride. The organic layer was recovered, and 25 g of silica gel was added. The resultant substance was stirred for 1 hour, the silica gel was removed with a 5 C filter, and the resultant substance was washed with 1000 g of chloroform. 60 g of activated carbon (Kuraray Coal GLC10/32) was added to the recovered chloroform solution, and the activated carbon was removed with a 5 C filter. The solvent was concentrated in vacuum. As a result, 54.75 g of mixture (monomer A3) of 2-hydroxy-3-methacryloyloxypropyl 3-hydroxy-1-adamantanecarboxylate, 1-hydroxy-3-methacryloyloxypropane-2-yl 3-hydroxy-1-adamantanecarboxylate, and 3-hydroxy-2-methacryloyloxypropyl 3-hydroxy-1-adamantanecarboxylate was obtained as a pale yellow viscous liquid (yield: 64.8%).

Comparative Example 4

3.05 g of mixture (monomer A3), which was obtained in monomer synthesis Example 1, of 2-hydroxy-3-methacryloyloxypropyl 3-hydroxy-1-adamantanecarboxylate, 1-hydroxy-3-methacryloyloxypropane-2-yl 3-hydroxy-1-adamantanecarboxylate, and 3-hydroxy-2-methacryloyloxypropyl 3-hydroxy-1-adamantanecarboxylate, 4.47 g of 2-ethyl-2-methacryloyloxyadamantane (monomer B1), 3.07 g of α-methacryloyloxy-γ-butyrolactone (C1), and 0.37 g of azobisisobutyronitrile were dissolved in 90 mL of tetrahydrofuran, and polymerization was performed for 15 hours while the reaction temperature was kept at 60° C. in a nitrogen atmosphere (the ratio of monomer amounts was A3/B1/C1=20/40/40 mol %). After the polymerization, the reaction solution was dripped into 450 mL of n-hexane to solidify and purify the generated resin. The generated white powder was filtrated and washed with 1000 ml of n-hexane. The white powder was recovered, and dried overnight at 40° C. at reduced pressure. As a result, 7.48 g of methacrylic copolymer P4 was obtained.

Synthesis Example 2 (Synthesis of Monomer A4)

A 100 ml three-necked round bottom flask provided with a stirrer, a thermometer and a distillation cooling device was supplied with 19.61 g (0.10 mol) of 3-hydroxyadamantane-1-carboxylic acid and 30.54 g (0.50 mol) of ethanolamine, and was heated to 150° C. The temperature was raised from 150° C. to 180° C. over 5 hours. During this time period, generated water was removed by distillation together with ethanolamine. After the reaction was finished, the resultant viscous liquid was dissolved in ethyl acetate, and the resultant solution was provided to fill a silica gel column. A top part of the solution was removed with ethyl acetate, and then the remaining part was fractionated and purified with a developing solvent, which was ethyl acetate/methanol=50/1 (v/v). The solvent was removed by distillation at reduced pressure. As a result, 12.25 g of 3-hydroxy-N-(2-hydroxyethyl)adamantane-1-carboxamide was obtained as a pale orange solid (yield: 51.2%).

Next, a 200 ml three-necked round bottom flask provided with a stirrer, a thermometer, and a cooling device was supplied with 10.00 g (41.8 mmol) of 3-hydroxy-N-(2-hydroxyethyl)adamantane-1-carboxamide obtained above, 1.02 g (8.32 mmol) of 4-dimethylaminopyridine, and 15.95 g (83.2 mmol) of 1-ethyl-3-(3-dimethylaminopropyl)carbodiimidehydrochloride. 7.16 g (83.2 mmol) of methacrylic acid was dissolved in 50 g of 1,2-dichloroethane, and the resultant substance was also supplied to the flask. The reaction solution was heated to 40° C. and stirred for 7 hours. Then, the heating was stopped, the temperature of the solution was lowered to room temperature, and the solution was stirred for 16 hours. After the reaction was finished, 150 ml of ethyl acetate was added, and the resultant solution was transferred to a 500 ml separatory funnel. The organic layer was washed with 100 g of ion exchange water, and organic layer (1) was recovered. The washing water was returned to the separatory funnel, 100 ml of ethyl acetate was added thereto, and organic layer (2) containing 2-(3-hydroxyadamantane-1-carboxamide)ethylmethacrylate was recovered. Organic layer (1) and organic layer (2) were mixed together, and 15 mg of p-methoxyphenol was added thereto. The solvent was concentrated in vacuum, and fractionated and purified by a silica gel column (developing solvent: chloroform/methanol=10/1 (v/v); Rf value: 0.35). 10 mg of p-methoxyphenol was added, and the solvent was removed by distillation. As a result, 7.31 g of 2-(3-hydroxyadamantane-1-carboxamide)ethylmethacrylate was obtained as a pale yellow solid (yield: 56.9%).

Comparative Example 5

3.08 g of 2-(3-hydroxyadamantane-1-carboxamide)ethylmethacrylate obtained in synthesis Example 2 (hereinafter, referred to as "monomer A4"), 4.97 g of 2-ethyl-2-methacryloyloxyadamantane (monomer B1), 3.40 g of α-methacryloyloxy-γ-butyrolactone (monomer C1), and 0.41 g of azobisisobutyronitrile were dissolved in 120 mL of tetrahydrofuran, and polymerization was performed for 15 hours while the reaction temperature was kept at 60° C. in a nitrogen atmosphere (the ratio of monomer amounts was A4/B1/C1=20/40/40 mol %). After the polymerization, the reaction solution was dripped into 600 mL of n-hexane to solidify and purify the resin. The generated white powder was filtrated with a membrane filter and washed with 1000 ml of n-hexane. The white powder was recovered, and dried overnight at 40° C. at reduced pressure. As a result, 8.12 g of methacrylic copolymer P5 was obtained.

Comparative Example 6

The same operation as in Example 6 was performed except that 2.12 g of 3-hydroxy-1-adamantylmethacrylate (hereinafter, referred to as "monomer A2") was used instead of monomer A1 (the ratio of monomer amounts was A2/B2/C2=20/40/40 mol %). As a result, 7.43 g of methacrylic copolymer P6 was obtained.

Examples 7 and 8, Comparative Examples 7 through 10

Formation of Resist Pattern 100 parts by weight of the methacrylic copolymer (each of P1 through P6) and 10 parts by weight of triphenylsulfoniumnonafluorobutanesulfonate (TPS-109 produced by Midori Kagaku Co., Ltd.) were dissolved in propyleneglycolmonomethyletheracetate (P) or ethyl lactate (L) such that the copolymer would have a concentration of 6.3% by weight. In this manner, a photosensitive resin composition was prepared (each of photosensitive resin compositions R1 through R6) (Table 1). A reflection-preventive film (ARC-29 produced by Nissan Chemical Industries, Ltd.) was applied to a silicon wafer, and the prepared resin composition for photoresist was applied to the reflection-preventive film by spin coating to form a photosensitive layer having a thickness of 100 nm. The photosensitive layer was prebaked at a temperature of 90° C. for 60 seconds on a hot plate, and then drawing was performed by an electron beam drawing device (ELS-7700 produced by Elionix Inc.) The resultant layer was post-baked (PEB) for 90 seconds at a temperature shown in Table 2, and then was developed for 60 seconds with an aqueous solution of 0.3 M of tetramethylammoniumhydroxide and rinsed with pure water to obtain a line-and-space pattern. The created line-and-space pattern was observed by an FE-SEM, and the exposure amount at which an image of 1:1 line-and-space pattern of 90 nm was resolved was set as the optimal exposure amount Eop ($\mu C/cm^2$). The minimum size of the 1:1 line-and-space pattern separately resolved at the optimal exposure amount was set as the limiting resolution. In addition, the line edge roughness (LER) was measured, and evaluated by a three-stage system (good, acceptable, or poor).

Table 1 shows the methacrylic copolymers and the solvents used in Examples 7 and 8 and comparative Examples 7 through 10. Table 2 shows the PEB temperature, Eop, LER, and limiting resolution.

TABLE 1

| | Copolymer used | Monomers used for copolymer (molar ratio) | Solvent used | Photosensitive resin composition |
|---|---|---|---|---|
| Example 7 | P1 | A1/B1/C1 (20/40/40) | P | R1 |
| Comparativ Example 7 | P3 | A2/B1/C1 (20/40/40) | P | R3 |
| Comparativ Example 8 | P4 | A3/B1/C1 (20/40/40) | L | R4 |
| Comparativ Example 9 | P5 | A4/B1/C1 (20/40/40) | L | R5 |
| Example 8 | P2 | A1/B2/C2 (20/40/40) | L | R2 |
| Comparativ Example 10 | P6 | A2/B2/C2 (20/40/40) | L | R6 |

TABLE 2

| | Photosensitive resin composition used | PEB temperature (° C.) | Optimal exposure amount Eop ($\mu C/cm^2$) | LER (nm) | Limiting resolution (nm) |
|---|---|---|---|---|---|
| Example 7 | R1 | 90 | 40 | Good | 75 |
| Comparative Example 7 | R3 | 100 | 40 | Good | 90 |
| Comparative Example 8 | R4 | 90 | 58 | Good | 90 |
| Comparative Example 9 | R5 | 110 | 58 | Good | 90 |
| Example 8 | R2 | 110 | 70 | Good | 80 |
| Comparative Example 10 | R6 | 120 | 70 | Good | 90 |

As seen from the results shown in Table 2, R1 and R2 as the photosensitive resin compositions in Examples 7 and 8 have characteristics superior to those of photosensitive resin compositions in the comparative examples. Specifically, photosensitive resin composition R1 in Example 7 was confirmed to allow the PEB temperature to be lowered and have a higher sensitivity to realize a lower limiting resolution as compared with photosensitive composition R3 in the corresponding comparative example. Photosensitive resin composition R2 in Example 8 was also confirmed to have a higher sensitivity as compared with photosensitive resin compositions R4 through R6 in the corresponding comparative examples. Comparative Examples 7 through 10 show good results regarding the LER (nm), but show poor results regarding at least either the optimal exposure amount Eop ($\mu C/cm^2$) or the limiting resolution (nm). Thus, comparative Examples 7 through 10 are not considered to provide good results when seen comprehensively.

The invention claimed is:

1. A (meth)acrylic ester compound expressed by general formula (1):

[Chemical formula 1]

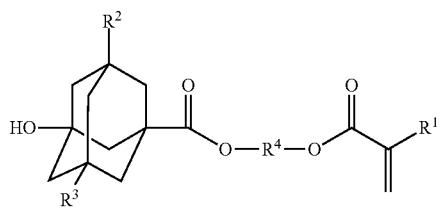

where $R^1$ represents a hydrogen atom or a methyl group, $R^2$ and $R^3$ may be the same as, or different from, each other and independently represent a hydrogen atom, a hydroxyl group, a cyclic, linear or branched alkyl group having a carbon number of 1 to 10, an aryl group, a cycloalkyl group, an alkoxy group having a carbon number of 1 to 10, an aryloxy group, an acyloxy group having a carbon number of 2 to 6, or a halogen group, and $R^4$ represents a linear or branched alkylene group having a carbon number of 2 to 5, wherein neither $R^2$ nor $R^3$ is a hydroxyl group or one of $R^2$ and $R^3$ is not a hydroxyl group.

2. A method for producing the (meth)acrylic ester compound according to claim 1, the method comprising reacting an adamantane compound expressed by general formula (2) with a hydroxyalkyl (meth)acrylate ester compound expressed by general formula (3) by use of a dehydration condensation agent:

[Chemical formula 2]

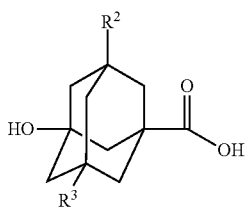

where $R^2$ and $R^3$ are the same as those in chemical formula (1);

[Chemical formula 3]

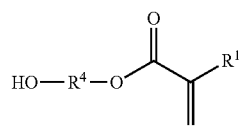

where $R^1$ and $R^4$ are the same as those in chemical formula (1).

3. The method according to claim 2, wherein the dehydration condensation agent is at least one selected from the group consisting of N,N'-dicyclohexylcarbodiimide, N,N'-diisopropylcarbodiimide, 1-ethyl-3-(3-dimethylaminopropyl)carbodiimide hydrochloride, 2,4,6-trichlorobenzoylchloride, 2-methyl-6-nitrobenzoic anhydride, 2,4,6-trichlorobenzoylchloride, bis(pentafluorophenyl) carbonate, and dimesitylammonium pentafluorobenzenesulfonate.

4. A (meth)acrylic copolymer, comprising a repeat unit expressed by general formula (4),

[Chemical formula 4]

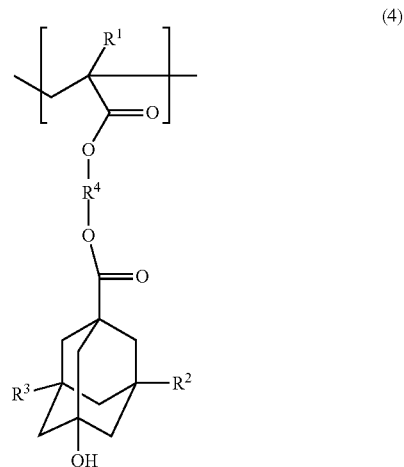

where $R^1$ represents a hydrogen atom or a methyl group, $R^2$ and $R^3$ may be the same as, or different from, each other and independently represent a hydrogen atom, a hydroxyl group, a cyclic, linear or branched alkyl group having a carbon number of 1 to 10, an aryl group, a cycloalkyl group, an alkoxy group having a carbon number of 1 to 10, an aryloxy group, an acyloxy group having a carbon number of 2 to 6, or a halogen group, and $R^4$ represents a linear or branched alkylene group having a carbon number of 2 to 5.

5. The (meth)acrylic copolymer according to claim 4, further comprising a repeat unit expressed by general formula (5) or (6) and a repeat unit expressed by general formula (7) or (8):

[Chemical formula 5]

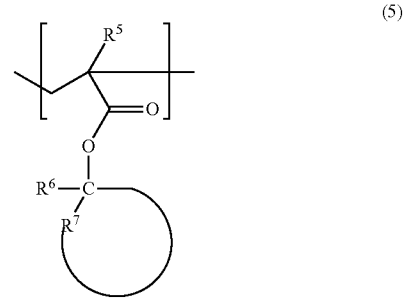

where $R^5$ represents hydrogen or a methyl group, $R^6$ represents an alkyl group having a carbon number of 1 to 4, and $R^7$ represents a linear or branched alkylene group having a carbon number of 5 to 20, or an alicyclic alkylene group;

[Chemical formula 6]

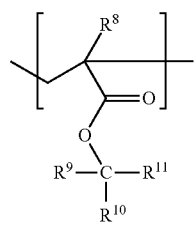

(6)

where $R^8$ represents hydrogen or a methyl group, $R^9$ and $R^{10}$ may be the same as, or different from, each other and each represent an alkyl group having a carbon number of 1 to 4, and $R^{11}$ represents an alkyl group having a carbon number of 1 to 4, a cycloalkyl group having a carbon number of 5 to 20, or an alicyclic alkyl group;

[Chemical formula 7]

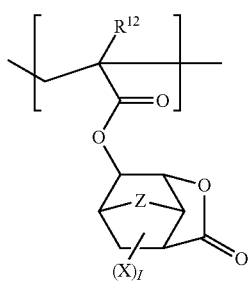

(7)

where $R^{12}$ represents hydrogen or a methyl group, Z represents methylene($-CH_2-$) or oxa($-O-$), X(s) may be the same as, or different from, each other and each represent a hydroxyl group, a halogen group, a nitrile group, a carboxylic acid group, an alkyl carboxylate group having a carbon number of 1 to 4, or an alkoxide group having a carbon number of 1 to 4, and I represents an integer of 0 to 2;

[Chemical formula 8]

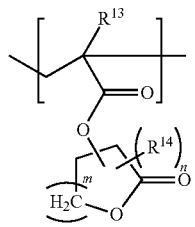

(8)

where $R^{13}$ represents hydrogen or a methyl group, m represents an integer of 1 to 3, $R^{14}$ represents a methyl group, an ethyl group, a hydroxyl group or a halogen group, and n represents an integer of 0 to 2.

6. A photosensitive resin composition, comprising the (meth)acrylic copolymer according to claim 4 and a photoacid generator.

* * * * *